(12) United States Patent
Pan

(10) Patent No.: US 7,305,719 B2
(45) Date of Patent: Dec. 11, 2007

(54) PROTECTIVE LENSES WITH A FLEXIBLE GASKET ASSEMBLY

(75) Inventor: Chen-Lieh Pan, Yilan Hsien (TW)

(73) Assignee: Water Square Sports Co., Ltd., Taipei Hsien (TW)

( * ) Notice: Subject to any disclaimer, the term of this patent is extended or adjusted under 35 U.S.C. 154(b) by 4 days.

(21) Appl. No.: 11/333,357

(22) Filed: Jan. 18, 2006

(65) Prior Publication Data

US 2007/0174951 A1 Aug. 2, 2007

(51) Int. Cl.
*A61F 9/02* (2006.01)
(52) U.S. Cl. .......................................... 2/430
(58) Field of Classification Search ............... 2/428, 2/430, 427
See application file for complete search history.

(56) References Cited

U.S. PATENT DOCUMENTS

| 5,585,869 A | * | 12/1996 | Weber | 351/83 |
| 6,082,857 A | * | 7/2000 | Lockhart | 351/178 |
| 6,341,863 B1 | * | 1/2002 | Chen-Lieh | 351/43 |
| 6,735,787 B2 | * | 5/2004 | Chen-Lieh | 2/428 |
| 6,736,136 B2 | * | 5/2004 | Chen-Lieh | 128/201.11 |
| 6,904,619 B2 | * | 6/2005 | Kuo | 2/426 |
| 7,172,278 B2 | * | 2/2007 | Feng | 351/43 |
| 2003/0142264 A1 | * | 7/2003 | Westerdal et al. | 351/106 |

* cited by examiner

*Primary Examiner*—Katherine Moran
(74) *Attorney, Agent, or Firm*—Troxell Law Office, PLLC

(57) ABSTRACT

Protective lenses with a flexible gasket assembly has a main lens, at least one peripheral lens, at least one hinge, a main lens gasket and at least one peripheral lens frame. Each hinge bonds to the main lens and one of the at least one peripheral lens to connect the main lens and the peripheral lens and provides a resilient cushion between the main lens and the peripheral lens to keep the lenses from breaking. The main lens gasket and the peripheral lens gasket are able to compensate for inaccuracies in the lenses prevent sharp edges on the lenses from injuring people.

2 Claims, 7 Drawing Sheets

PROTECTIVE LENSES WITH A FLEXIBLE GASKET ASSEMBLY

BACKGROUND OF THE INVENTION

1. Field of the Invention

The present invention relates to protective lenses, and more particularly to protective lenses with a flexible gasket assembly that have a wide field of view and high safety factor.

2. Description of Related Art

Masks and goggles are widely used in many fields such as water activities, biking, snow sports and any other activities that require eye protection.

Conventional eye protection devices comprise a lens frame and lenses. The lenses are mounted in the main frame. The conventional lenses may be a one-piece lens or two lenses. The one-piece lens and the two lenses are made of essentially flat optical material such as glass or plastic. When a person wears the eye protection device, the essentially flat lens and the lens frame limit the person's field of view so that the person's peripheral vision is virtually completely obstructed.

To overcome this problem, an eye protection device with a wide field of view was developed. A conventional eye protection device with a wide field of view comprises a main frame, a main lens, two peripheral lenses and two lens connectors. The main lens and the peripheral lenses are mounted in the main frame. The lens connectors are relatively narrow and are mounted between the main lens and peripheral lenses to connect the peripheral lenses to the main lens at an angle to unmask a person's peripheral vision.

When a person wears the eye protection device with a wide field of view, the person can see through the main lens and the peripheral lenses. Furthermore, the lens connectors between the main lens and the peripheral lenses are thin line obstructions to the person's vision.

The lens connectors can also make the main frame, the lens and the peripheral lenses waterproof, but the lens connectors cannot allow the main frame, the main lens and the peripheral lenses to change shapes or be adjusted. When a force acts on the eye protection device with a wide field view, the main lens and the peripheral lenses are easily broken. To keep the lenses from breaking, the lens frame has to be strong and large, which makes the lens frame heavy and inconvenient to use.

All lenses need to be cut to a specific size before the eye protection devices are assembled. However, every lens cannot be cut precisely enough to make every lens exactly the same. Because the lens connectors are only mounted between the main lens and the peripheral lenses, the lens connectors cannot be adjusted or compensate for imprecision in the lenses after cutting. Furthermore, imprecision in the cutting of lenses will result in variations in assembly of the eye protection devices. If the lenses sizes are larger than the precise size, the connector will break away between the main lens and the peripheral lens when a force is applied to the lenses. If the lenses are smaller than the precise size, leaks will develop between the lenses and the lens frame when a force is applied to the lenses. After cutting, edges of the lenses are sharp and easily injury a person or cause the lenses to break.

To overcome the shortcomings, the present invention provides protective lenses with a flexible gasket assembly to obviate or mitigate the aforementioned problems.

SUMMARY OF THE INVENTION

The primary objective of the present invention is to provide protective lenses with a flexible gasket assembly so that an eye protection device has a wide field of view, a high safety factor and accurate assembly.

The protective lenses with a flexible gasket assembly has a main lens, at least one peripheral lens, at least one hinge, a main lens gasket and at least one peripheral lens gasket. The hinge bonds to the main lens and one of the at least one peripheral lens to connect the peripheral lens to the main lens and provides a resilient cushion between the main lens and the peripheral lens. The resilient cushion keeps adjacent lenses from breaking each other when a force is applied to the lenses. The main lens gasket is the same resilient material as the hinge, is bonded around the main lens and is connected to the hinge. The resilient material compensates for any inaccuracy in the main lens and prevents sharp edges from injuring people. The peripheral lens gasket is the same resilient material as the hinge, is bonded around the peripheral lens and is connected to the hinge. The resilient material compensates for any inaccuracy in the peripheral lens and prevents sharp edges from injuring people. Consequently, the hinge, the main lens gasket and the peripheral lens gasket provide a high safety factor and facilitate accurate assembly of an eye protection device.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
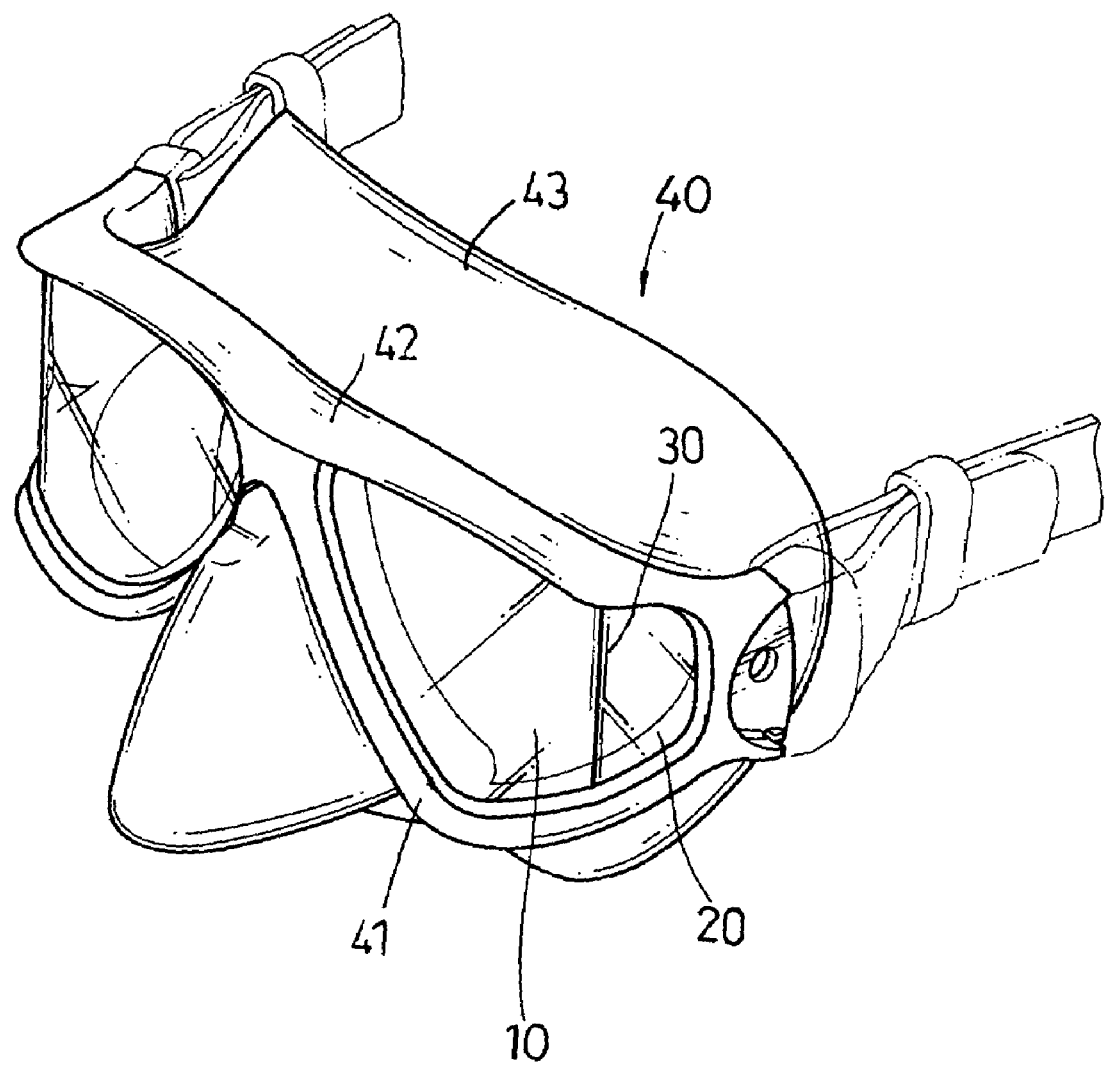
FIG. 1 is a perspective view of a first embodiment of protective lenses with a flexible gasket assembly in accordance with the present invention in an eye protection device.
Figure 2:
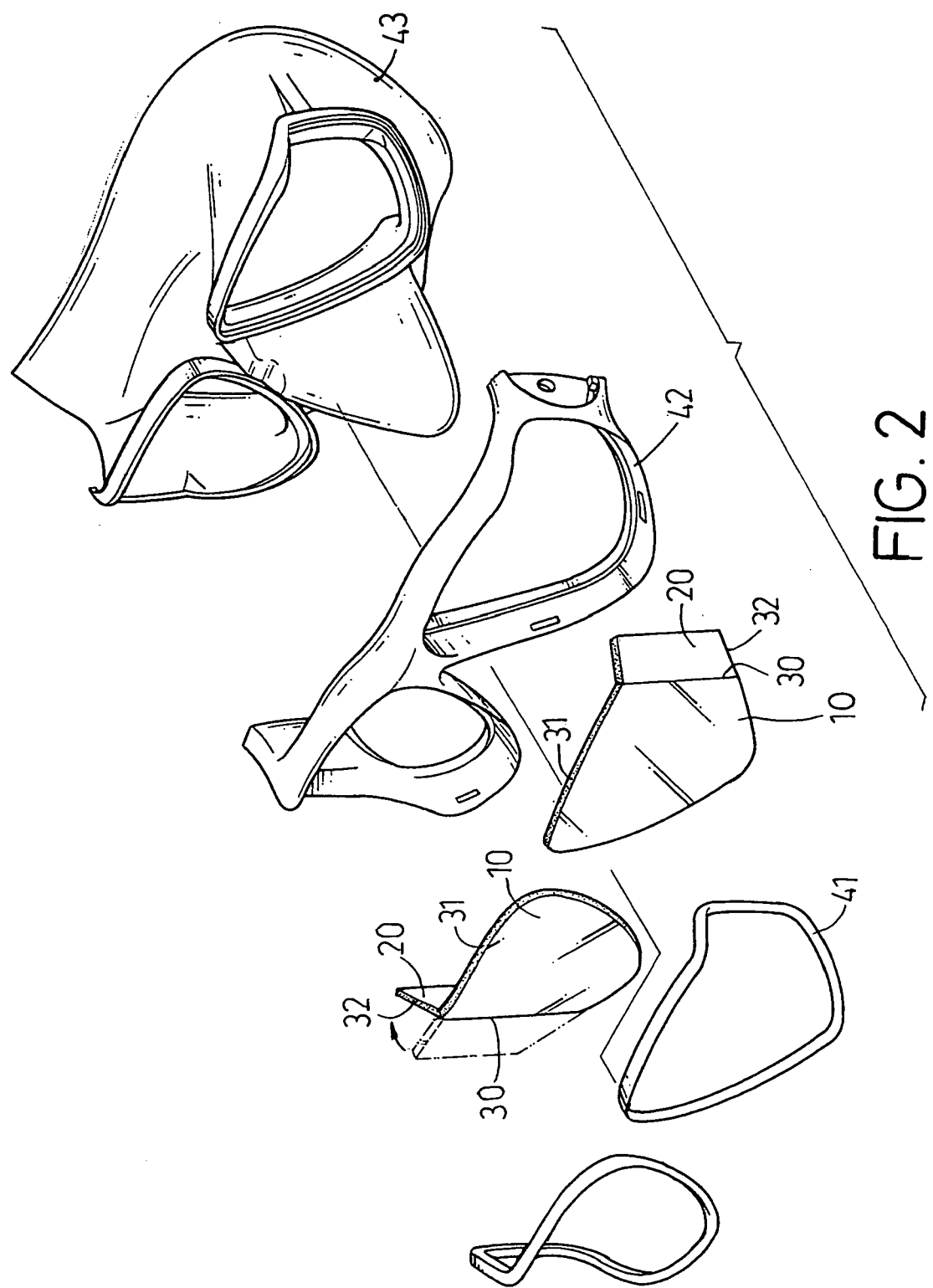
FIG. 2 is an exploded perspective view of the protective lenses with a flexible gasket assembly in FIG. 1.

With reference to FIGS. 1, 2, 9 and 10, an eye protection devices (40, 40A, 40B) comprises at least one lens retainer (41, 41A, 41B), multiple lenses (10, 10A, 10B, 20, 20A, 20B, 20C), a lens frame (42, 42A, 42B) and a skirt (43, 43A, 43B).

With further reference to FIGS. 3, 4, 5, 6, 9 and 10, protective lenses with a flexible gasket assembly in accordance with the present invention comprises multiple lenses (10, 10A, 10B, 20, 20A, 20B, 20C), at least one hinges (30, 30A, 30B, 30C), a main lens gasket (31) and at least one peripheral lens gasket (32).

Figure 3:
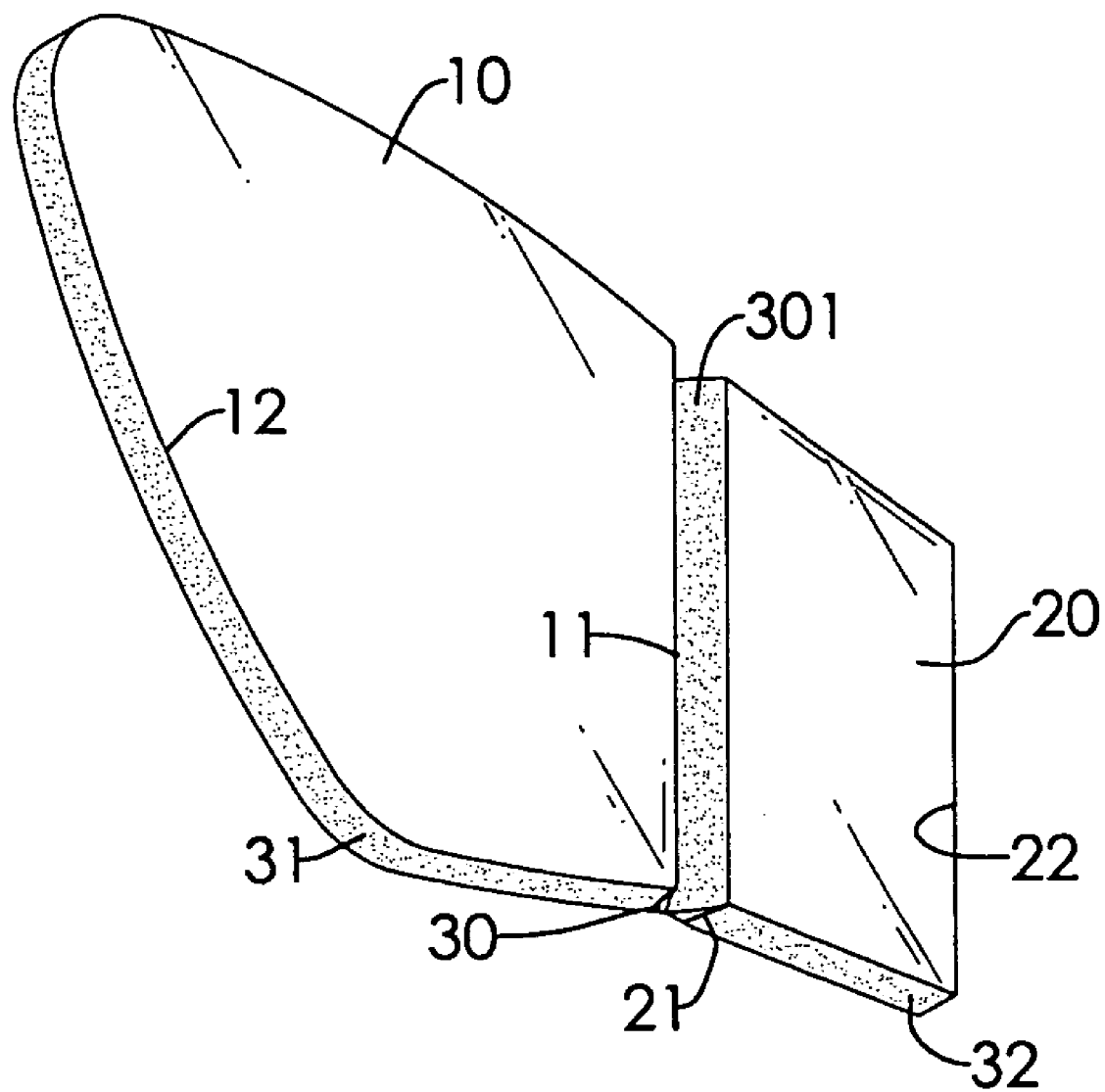
FIG. 3 is a perspective view of the protective lenses with a flexible gasket assembly in FIG. 2 on a main lens and a peripheral lens.
Figure 4:
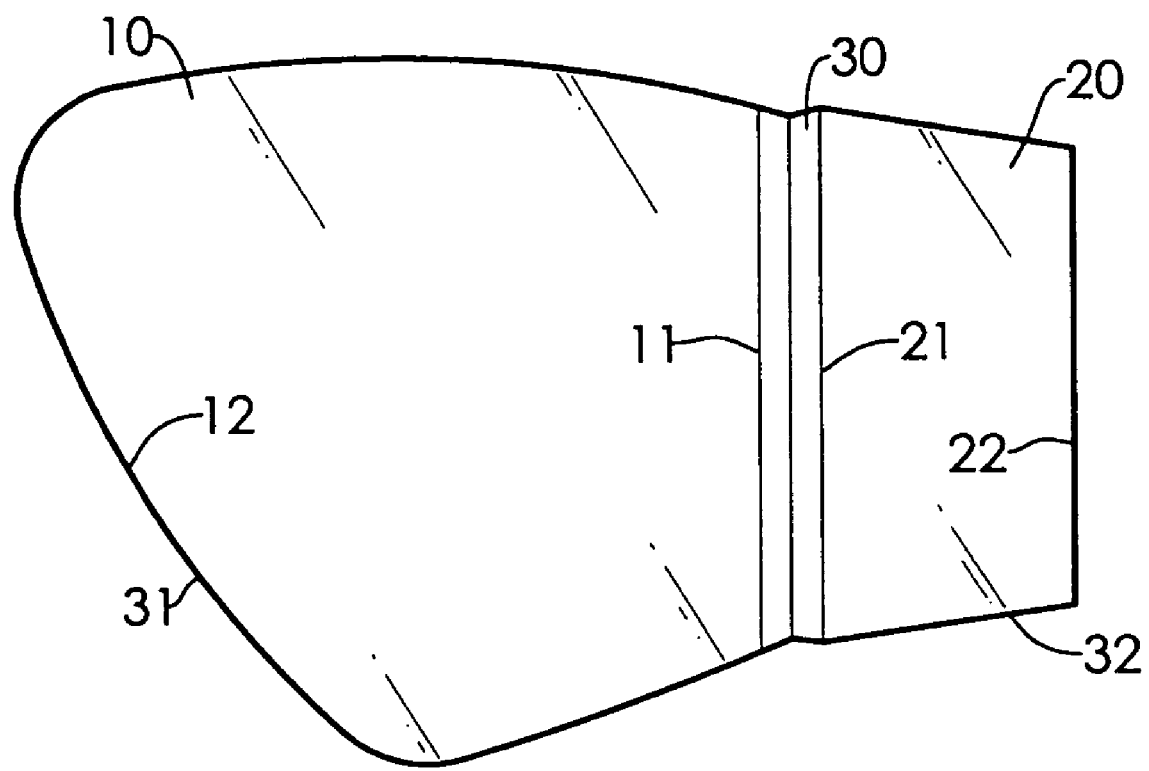
FIG. 4 is rear view of the protective lenses with a flexible gasket assembly in FIG. 2 on a main lens and a peripheral lens.
Figure 5:
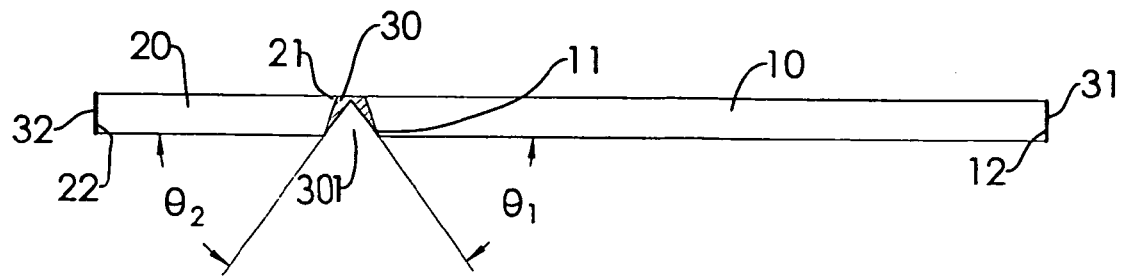
FIG. 5 is top view of a hinge of the protective lenses with a flexible gasket assembly in FIG. 2 on a main lens and a peripheral lens.

With further reference to FIG. 3, the lenses (10, 10A, 10B, 20, 20A, 20B, 20C) comprise a main lens (10, 10A, 10B) and at least one peripheral lens (20, 20A, 20B, 20C). The main lens (10, 10A, 10B) has multiple outer edge segments (11, 12). The outer edge segments (11, 12) are formed around the main lens (10, 10A, 10B) and comprise a linear hinge edge (11) and a gasket edge (12). The linear hinge edge (11) has two ends, and the gasket edge (12) is formed around the main lens (10, 10A, 10B) and connects to the two ends of the linear hinge edge (11). Each peripheral lens (20, 20A, 20B, 20C) has multiple outer edge segments (21, 22). The outer edge segments (21, 22) are formed around the peripheral lens (20, 20A, 20B, 20C) and comprise a linear hinge edge (21) and a gasket edge (22). The linear hinge edge (21) corresponds to the linear hinge edge (11) on the main lens (10, 10A, 10B) and has two ends. The gasket edge (12) is formed around the peripheral lens (20, 20A, 20B, 20C) and connects to the two ends of the linear hinge edge (21).

Figure 7:
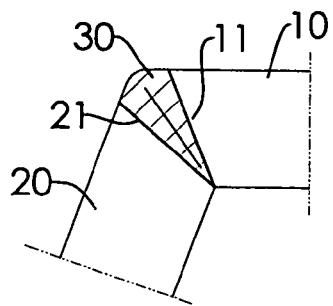
FIG. 7 is an enlarged operational top view in partial section of the hinge of the protective lenses with a flexible gasket assembly in FIG. 2 when a main lens and a peripheral lens fold together.
Figure 6:
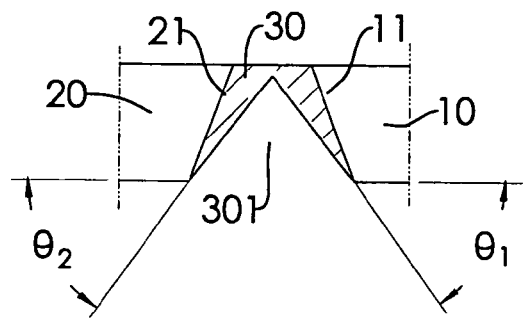
FIG. 6 is an enlarged top view in partial section of the hinge of the protective lenses with a flexible gasket assembly in FIG. 2 on a main lens and a peripheral lens.
Figure 8:
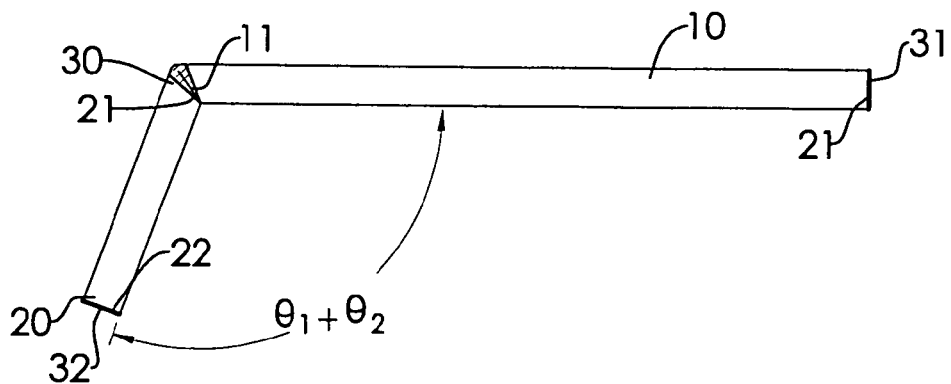
FIG. 8 is a top view of the protective lenses with a flexible gasket assembly in FIG. 7 when the main lens and the peripheral lens fold together.

With further reference to FIGS. 7 and 8, the hinge (30, 30A, 30B, 30C) is bonded to a linear hinge edge (11) of the main lens (10, 10A, 10B) and the corresponding linear hinge edge (21) of the peripheral lens (20, 20A, 20B, 20C) to connect the peripheral lens (20, 20A, 20B, 20C) to the main lens (10, 10A, 10B) and has a V-shaped groove (301). The V-shaped groove (301) is formed formed longitudinally in the hinge (30, 30A, 30B, 30C) to allow the hinge (30, 30A, 30B, 30C) to bend to a specific angle ($\ominus_1 + \ominus_2$) and has two inner surfaces, an interior angle and two outer surfaces. One of the inner surfaces of the V-shaped groove (301) adjacent to the linear hinge edge (11) of the main lens (10, 10A, 10B) inclined relative to the main lens (10, 10A, 10B) at a first angle $\ominus_1$. The other inner surface of the V-shaped groove (301) adjacent to the linear hinge edge (21) of the at least one peripheral lens (20, 20A, 20B, 20C) is inclined relative to the at least one peripheral lens (20, 20A, 20B, 20C) at a second angle of $\ominus_2$. The interior angle is formed between the two inner surfaces. The angle of the V-shaped groove (301) is $180° - \ominus_1 - \ominus_2$. The V-shaped groove (301) allows the main lens (10, 10A, 10B) and the at least one peripheral lens (20, 20A, 20B, 20C) to fold to an angle of $\ominus_1 - \ominus_2$. The outer surfaces are bonded respectively to the linear hinge edge (11) of the main lens (10, 10A, 10B) and the corresponding linear hinge edge (21) of the peripheral lens (20, 20A, 20B, 20C).

The main lens gasket (31) is bonded to the gasket edge (12) of the main lens (10, 10A, 10B) and attaches to the at least one hinge (30).

The at least one peripheral lens gasket (32) is bonded respectively to the gasket edge (22) of the at least one peripheral lens (20, 20A, 20B, 20D) and attach respectively to the corresponding hinges (30). When the main lens (10, 10A, 10B) and the at least one peripheral lenses (20, 20A, 20B, 20D) fold toward each other, the hinges (30) keep the main lens (10, 10A, 10B) and the at least one peripheral lens (20, 20A, 20B, 20D) at a specific angle, $\ominus_1 + \ominus_2$.

Figure 9:
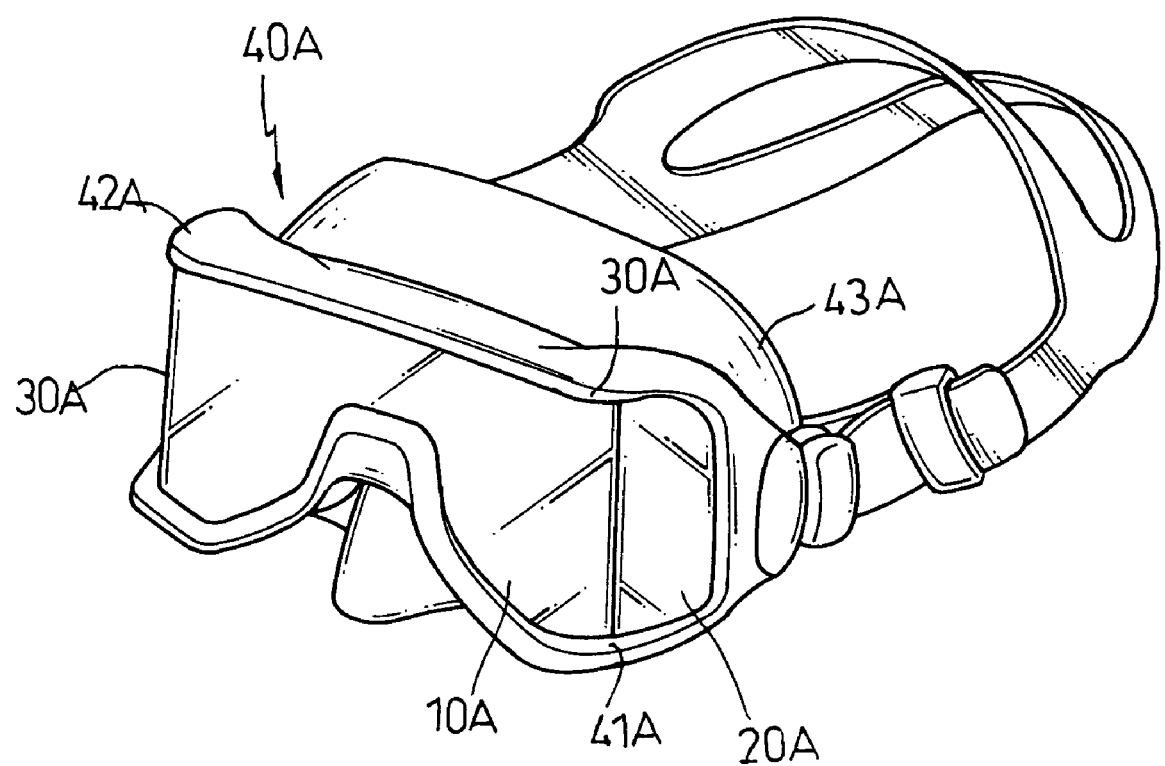
FIG. 9 is a perspective view of a second embodiment of protective lenses with a flexible gasket assembly in accordance with the present invention on another eye protection device.

With further reference to FIG. 9, a second embodiment of a flexible gasket assembly for protective lenses in accordance with the present invention, at least two peripheral lens (20A) attach to one of the main lens (10A) so that two hinges (30A), at least two peripheral lens gaskets and the main lens gasket separately attach to the peripheral lenses (20A) and the main lens (10A). The two hinges (30A) connect separately to two sides of the main lens frame and one of peripheral lens gaskets connect to one of the hinges (30A).

Figure 10:
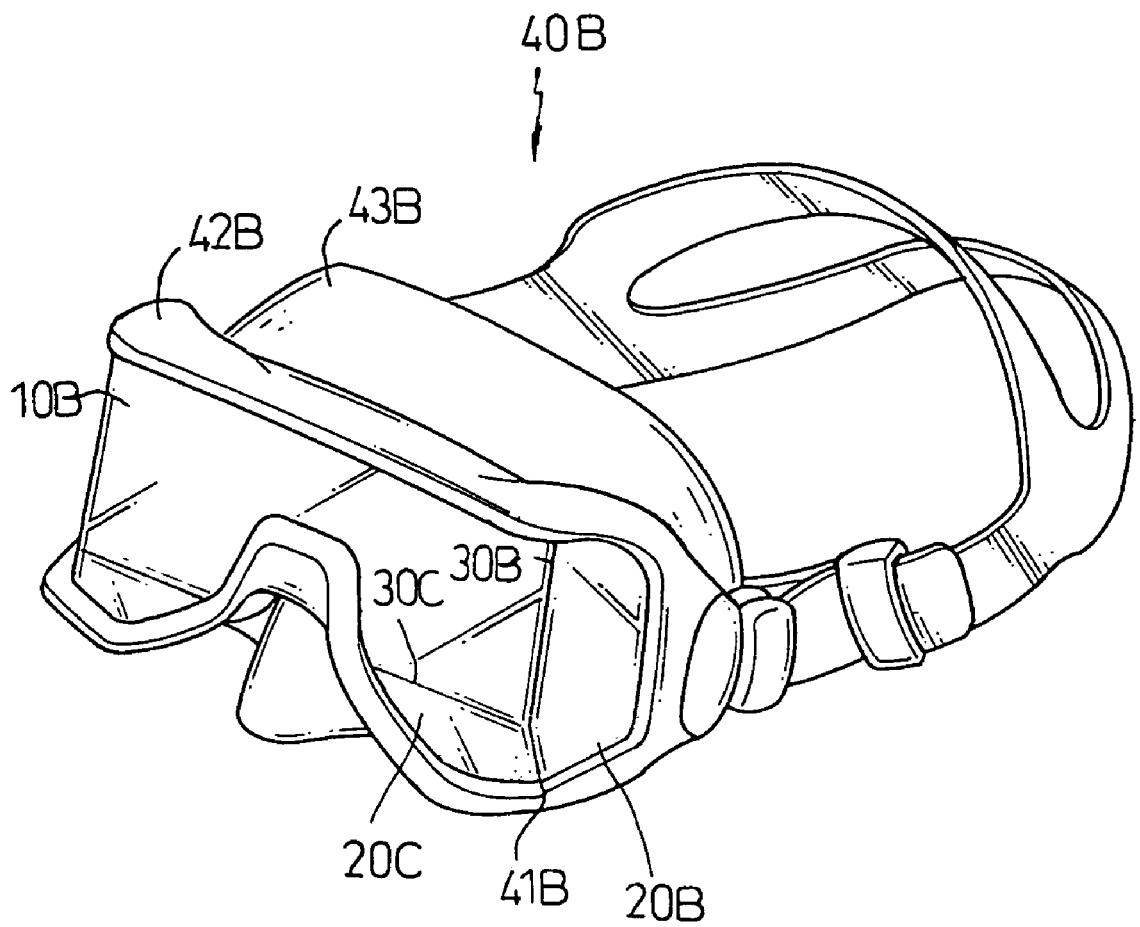
FIG. 10 is a perspective view of a third embodiment of protective lenses with a flexible gasket assembly in accordance with the present invention on another eye protection device.

With further reference to FIG. 10, a third embodiment of second embodiment of a flexible gasket assembly for protective lenses in accordance with the present invention, four the peripheral lenses (20B, 20C) attach to one main lens (10B) so that four hinges (30B, 30C), peripheral lens gaskets and one main lens gasket attach to the peripheral lens (20B, 20C) and the main lens (10B). The four hinges (30B, 30C) connect separately to two sides and two bottoms of the main lens.

When a force acts on the eye protecting device (40, 40A, 40B), the hinge (30, 30A, 30B, 30C) is able absorb the force and acts as a cushion so the lenses (10, 10A, 10B, 20, 20A, 20B, 20D) are not broken. Furthermore, the main lens gasket (31) and the peripheral lens gasket (32) compensate for differences in the lenses (10, 10A, 10B, 20, 20A, 20B, 20D) to keep leaks from developing between the lenses (10, 10A, 10B, 20, 20A, 20B, 20D) and the eye protection device (40, 40A, 40B) cover any sharp edges of the lenses (10, 10A, 10B, 20, 20A, 20B, 20D) to keep people from being injured.

Even though numerous characteristics and advantages of the present invention have been set forth in the foregoing description together with details of the structure and function of the invention, the disclosure is illustrative only. Changes may be made in detail especially in matters of shape, size, and arrangement of parts within the principles of the invention to the full extent indicated by the broad general meaning of the terms in which the appended claims are expressed.

What is claimed is:

1. Protective lenses with a flexible gasket assembly comprising:
    a main lens with a linear hinge edge and a gasket edge;
    at least one peripheral lens with a linear hinge edge and a gasket edge;
    a main lens gasket bonded to the gasket edge of the main lens;
    at least one peripheral lens gasket bonded to the gasket edge of the at least one peripheral lens; and
    at least one hinge, and each one of the at least one hinge having two outer surfaces being bonded respectively to the linear hinge edge of the main lens and the linear hinge edge of a corresponding peripheral lens; and
    a groove longitudinally formed in the hinge, having two inner surfaces being attached to each other to connect the corresponding peripheral lens to the main lens and allowing the main lens and the corresponding peripheral lens to fold to an angle.

2. The protective lenses as claimed in claim 1, wherein each groove is V-shaped.

* * * * *